United States Patent [19]
Petrie et al.

[11] Patent Number: 5,361,416
[45] Date of Patent: Nov. 8, 1994

[54] HEADCOVER AND CHIN STRAP FOR TREATING SLEEP APNEA

[76] Inventors: Steven C. Petrie, 245 Bandra Dr.; Roger C. Petrie, 1925 Melrose #3, both of Walla Walla, Wash. 99362

[21] Appl. No.: 152,694

[22] Filed: Nov. 16, 1993

[51] Int. Cl.$^5$ .............................................. A42B 1/00
[52] U.S. Cl. ........................................ 2/171.2; 2/171; 2/421; 602/902
[58] Field of Search ................. 2/171, 171.2, 410, 417, 2/418, 419, 420, 421, 425, 909, 918, DIG. 11; 128/201.22, 201.23, 201.24, 206.27, 206.28, 848; 602/74, 75, 902

[56] References Cited

U.S. PATENT DOCUMENTS

| | | | |
|---|---|---|---|
| 1,519,915 | 12/1924 | Johnson | 602/902 |
| 1,587,558 | 6/1926 | Sheffield | 602/902 |
| 2,416,411 | 2/1947 | Sharbaugh et al. | 128/206.27 |
| 3,513,482 | 5/1970 | Holden | 2/421 |
| 3,776,244 | 12/1973 | Morgan | 2/171.2 |
| 4,051,556 | 10/1977 | Davenport et al. | 2/421 |
| 4,651,356 | 3/1987 | Zide | 2/421 |
| 4,692,947 | 9/1987 | Black et al. | 2/425 |
| 4,766,610 | 8/1988 | Mattes | 2/909 |

Primary Examiner—Clifford D. Crowder
Assistant Examiner—Diana L. Biefeld
Attorney, Agent, or Firm—Richard C. Litman

[57] ABSTRACT

A headcover and chin cup assembly which maintains a closed mouth during the treatment of sleep apnea and makes the user breathe only through his or her nose. The assembly is made up of a headcover which fits easily and securely on the head of practically all people. The headcover and the chin cup each include a set of straps and a set of D-rings. The set of straps attached to the headcover engage the set of D-rings attached to the chin cup. The set of straps attached to the chin cup engage the set of D-rings attached to the headcover. Each set of straps is adjusted secured via fasteners. The chin cup holds the apex of the user's chin for a secure fit.

6 Claims, 2 Drawing Sheets

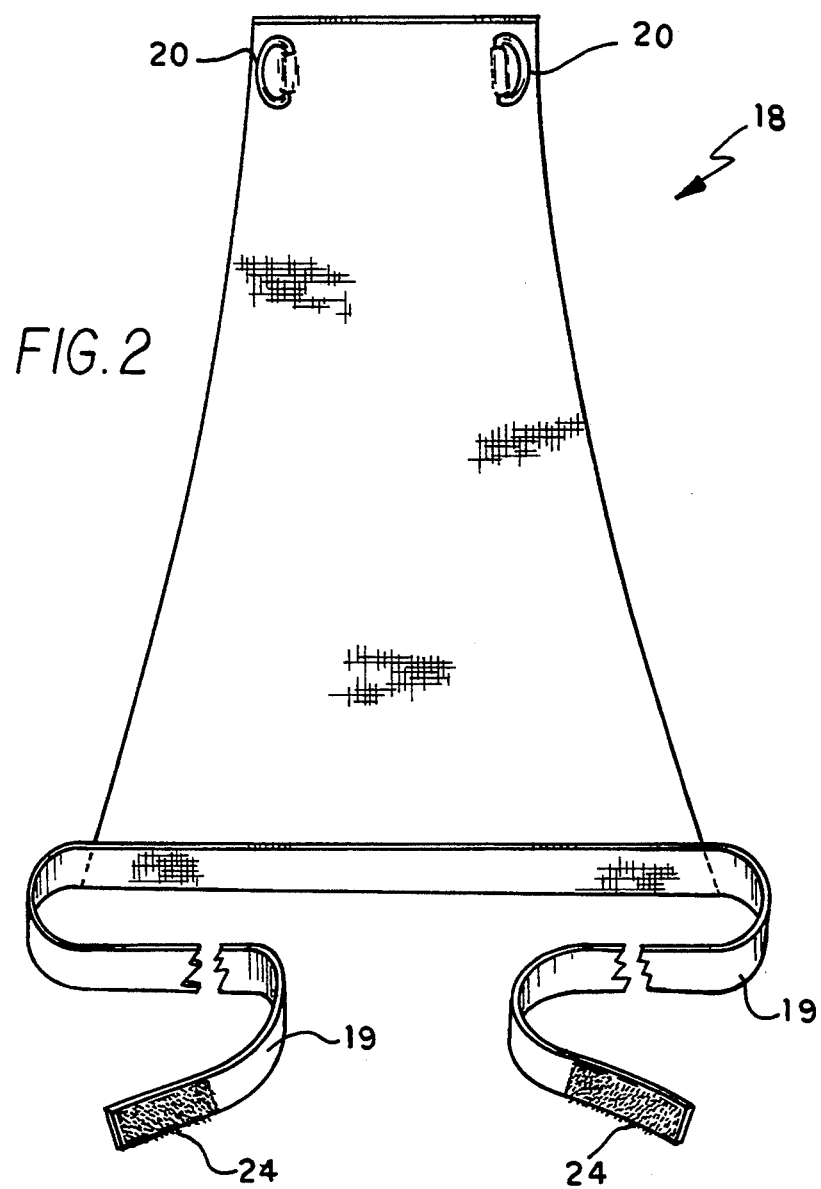
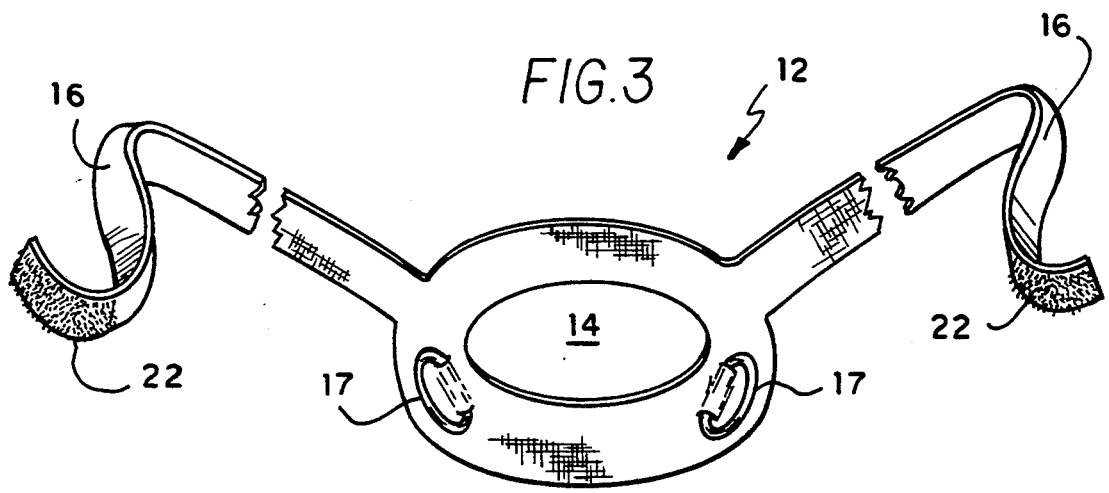

HEADCOVER AND CHIN STRAP FOR TREATING SLEEP APNEA

BACKGROUND OF THE INVENTION

1. Field of the Invention

The present invention relates to devices for treating sleep disorders and, more particularly, to a headcover and chin strap assembly which is to be used to aid in the treatment of sleep apnea. At the present time, correctors using chin straps are cumbersome and uncomfortable to use.

2. Description of the Prior Art

Devices including chin straps are used for both corrective and protective measures. However, known chin straps are adjusted and secured via complex fasteners. For example, U.S. Pat. No. 1,519,915, issued Dec. 16, 1924 to Walter G. Johnson, discloses a corrective mouth breather having a chin strap with a chin cup in combination with a mouth closure and a plurality of straps for forcing a user to breathe only through the nose. Similar to that of the foregoing corrective mouth breather is the jaw bracing and setting appliance shown in U.S. Pat. No. 1,587,558, issued Jun. 8, 1926 to Elise H. Sheffield. Sheffield discloses an appliance having a chin strap with a chin cup. The chin cup has a oval shaped aperture in which the apex of the chin is placed and two straps for securing the device to the user. A retention device shown in U.S. Pat. No. 3,776,244, issued Dec. 4, 1973 to Willis E. Morgan. Morgan discloses non-slip retention means using a chin strap secured by a plurality of straps via hook and loop fasteners. Yet nother chin strap is shown in U.S. Pat. No. 3,572,329, issued on Mar. 23, 1971 to Irvin S. De Woskin, who discloses a chin strap with two straps for securing it to a protective headgear.

Unlike that shown in the aforementioned patents, U.S. Pat. No. 4,651,356, issued Mar. 24, 1987 to Robert M. Zide, discloses a helmet chin strap with a chin cup secured via four straps. Another helmet chin strap is disclosed in U.S. Pat. No. 5,123,121, issued Jun. 23, 1992 to Lester V. Broersma. Broersma discloses a helmet retention system with straps that are adjustably engaged via glide rings.

Another patent deemed of interest includes U.S. Pat. No. 5,183,059, issued Feb. 2, 1993 to David Leonardi, who discloses an eye shield retention system with straps looped through eyelets and secured via hook and loop fasteners.

None of the above inventions and patents, taken either singly or in combination, is seen to describe the instant invention as claimed.

SUMMARY OF THE INVENTION

The present invention relates to a chin strap which is used to aid in the treatment of sleep apnea. The chin strap keeps a user's mouth shut, thus insuring a patient will breathe through his nose.

Sleep apnea results in the reduction of the amount of air being inhaled into the lungs. This is sometimes the direct result of breathing through the mouth rather the nose. Breathing through the mouth causes an open loop resulting in a loss of air pressure via air leaking out from the nose. When the mouth is shut and breathing occurs through the nose, the loop is closed causing no loss in air pressure.

When treating a patient with sleep apnea, often the patient is connected to a Continuous Positive Airway Pressure (CPAP) device or a Bidirection Positive Airway Pressure (BiPAP) via a mask to fit snugly around the nose. A hose is connected to the mask to blow air into the nose at a set pressure. The appropriate air pressure is determined in a trial and error fashion.

For the treatment of sleep apnea to be effective, the patient's mouth must be kept shut. To insure this, an adjustable chin strap is used to insure proper air flow to the lungs.

Accordingly, it is a principal object of the invention to aid in the treatment of sleep apnea by providing a chin strap which maintains a closed mouth to insure the patient breathes only through his nose when sleeping.

It is another object of the invention to provide a chin strap with a headcover which fits easily and securely on the head of practically all people.

It is a further object of the invention to provide a plurality of straps which are adjusted via D-rings and secured via fasteners.

Still another object of the invention is to provide a chin cup to hold the apex of the user's chin for a secure fit.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a rear elevational view of the headcover shown somewhat in perspective.

FIG. 3 is a front elevational view of the chip strap shown somewhat in perspective.

Similar reference characters denote corresponding features consistently throughout the attached drawings.

DETAILED DESCRIPTION OF THE PREFERRED EMBODIMENT

Figure 1:
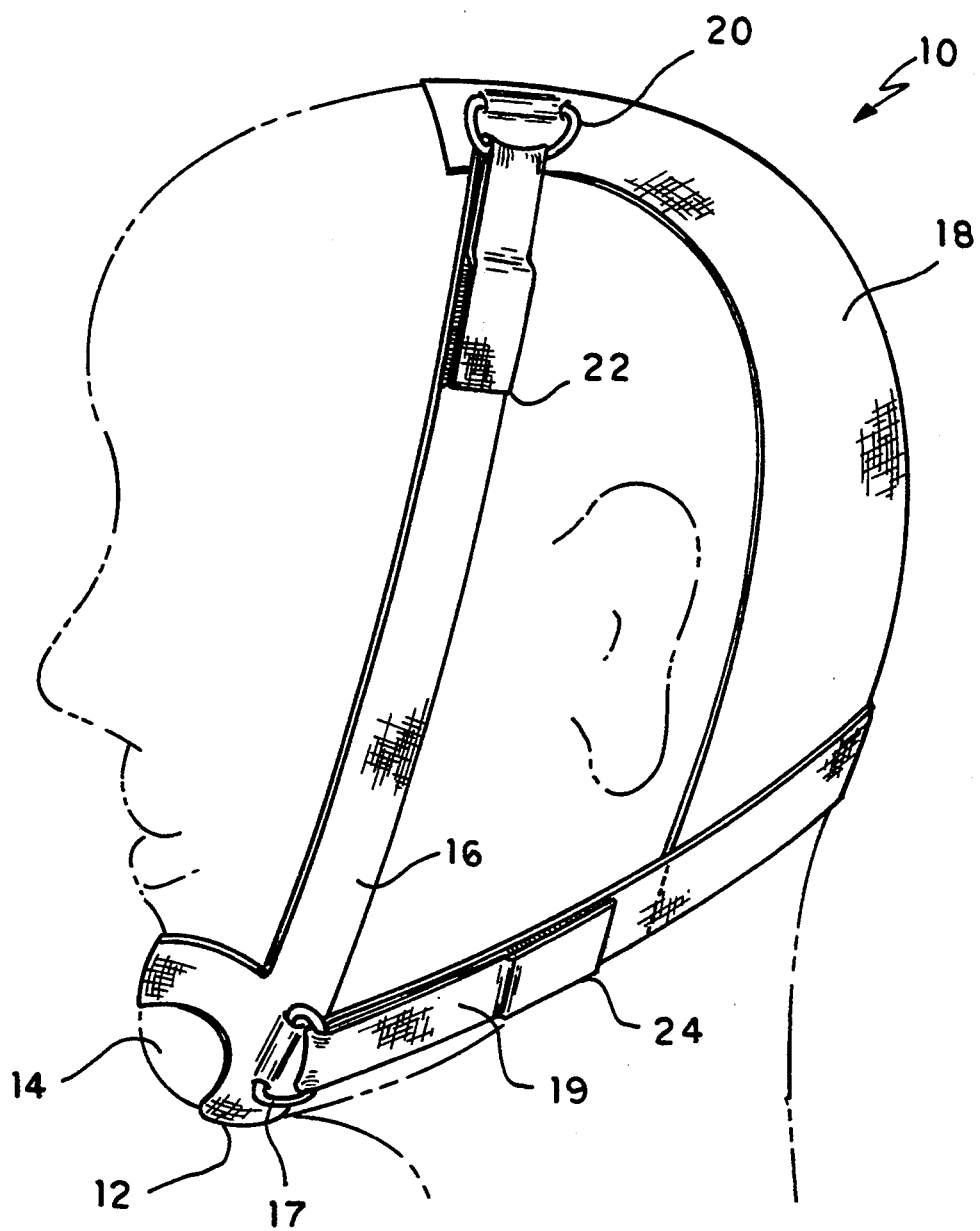
FIG. 1 is an environmental side elevational view of the chin strap as worn on the head of a user.

Referring to FIG. 1, chin strap 10 is shown being worn by a user of the device. The chin strap 10 includes a chin strap cup 12 in which a user places his chin. Two straps 16 and two D-rings 17, are fixedly attached to the chin strap cup 12, as are shown more clearly in FIG. 3. The chin strap cup 12 further includes an aperture 14 for engaging the apex of the chin of the user. The aperture 14 provides a secure and comfortable fit of the chin strap cup 12.

A headcover 18 is worn by the user. The headcover 18 is placed on the crown of the head of the user and drapes over the nape of the neck of the user. Two straps 19 and two D-rings 20 are fixedly attached to the headcover 18, as are shown more clearly in FIG. 2. Each strap 16, 19 is slipped through a respective D-rings 20, 17. Straps 16 extend from the sides of the chip strap cup 12 and provide an upward force to keep the user's mouth closed. Straps 19 extend from the corners of headcover 18 draped over the user's nape and hold the headcover 18 in place to prevent slippage of the headcover 18. D-rings 20 are at the corners of headcover 18 resting on the crown of the user's head. D-rings 17 are at the sides of the chip strap cup 12.

The straps 16, 19 are slidably adjusted through respective D-rings 20, 17. Once straps 16, 19 are adjusted according to the comfort of the user, each strap 16, 19 is doubled back against itself and is secured to itself via matingly engageable hook and loop fasteners 22, 24. The fasteners 22, 24 are preferably hook and loop fasteners but can be any type of fasteners which maintain straps 16, 19 in a secured position.

Referring now to FIG. 2, headcover 18 is shown with D-rings 20 and straps 19. The narrow portion of headcover 18 is placed on the crown of the user's head. The wide portion of headcover 18 is draped over the user's nape.

Lastly, referring to FIG. 3, the chin strap cup 12 with aperture 14 has D-rings 17 and straps 16 fixedly attached to it.

The D-rings 17, 20 facilitate adjustment of each strap 16, 19 when chin strap 10 is being worn. Fasteners 22, 24 are used to secure each strap 16, 19 individually to insure a proper fit.

It is to be understood that the present invention is not limited to the sole embodiment described above, but encompasses any and all embodiments within the scope of the following claims.

I claim:

1. A headcover and chin strap assembly to aid in the treatment of sleep apnea comprising:
   cup means for engaging a chin, said cup means including a first set of D-rings;
   headcover means for supporting said cup means, said headcover means including a top, a rear, and a second set of D-rings located proximate to said top, said headcover means being proportioned so that said top covers a crown and said rear covers a nape of a user; and
   a first set of straps extending from said cup means for adjustably engaging said second set of D-rings of said headcover means,
   a second set of straps extending from the rear of said headcover means for adjustably engaging said first set of D-rings of said cup means.

2. An assembly according to claim 1, wherein:
   said cup means includes a bottom region, and said bottom region has an aperture.

3. An assembly according to claim 2, wherein:
   said aperture in said cup means is oval shaped.

4. An assembly according to claim 1, wherein:
   each said strap is secured via fastening means.

5. An assembly according to claim 4, wherein:
   said fastening means are hook and loop fasteners.

6. A head cover and chin strap assembly to aid in the diagnosis and treatment of sleep apnea comprising:
   a chin cup having a center and including a first set of straps and a first set of D-rings attached thereto, said center of said cup means further having an oval shaped aperture;
   a unitary trapezoidal headcover having a first side and an opposite side, wherein said first side has a length substantially longer than said opposite side, said headcover further including a second set of straps proximate to the first side and a second set of D-rings proximate to the opposite side, said second set of straps being engagable with said first set of D-rings and said first set of straps being engagable with said second set of D-rings;
   said first set of straps extending from said chin cup means for adjustably engaging said second set of D-rings attached to said headcover, said second set of straps extending from said headcover for adjustably engaging said first set of D-rings attached to said chin cup.

* * * * *